US00PP19193P2

(12) United States Plant Patent
Larsen

(10) Patent No.: US PP19,193 P2
(45) Date of Patent: Sep. 9, 2008

(54) ***OSTEOSPERMUM* PLANT NAMED 'SUNNY BIANCA'**

(50) Latin Name: *Osteospermum ecklonis*
Varietal Denomination: Sunny Bianco

(75) Inventor: Bjarne Nyholm Larsen, Odense N. (DK)

(73) Assignee: Sunny grönnegyden APS, Odense (DK)

( * ) Notice: Subject to any disclaimer, the term of this patent is extended or adjusted under 35 U.S.C. 154(b) by 0 days.

(21) Appl. No.: 11/821,111

(22) Filed: Jun. 20, 2007

(51) Int. Cl.
*A01H 5/00* (2006.01)

(52) U.S. Cl. ..... Plt./360

(58) Field of Classification Search ..... Plt./360
See application file for complete search history.

(56) References Cited

U.S. PATENT DOCUMENTS

PP16,564 P3 * 5/2006 Larsen ..... Plt./360

* cited by examiner

*Primary Examiner*—Wendy C. Haas
(74) *Attorney, Agent, or Firm*—C. A. Whealy

(57) ABSTRACT

A new and distinct cultivar of *Osteospermum* plant named 'Sunny Bianca', characterized by its upright and mounded plant habit; freely branching growth habit; freely flowering habit; daisy-type inflorescences with oblanceolate-shaped ray florets that are initially whitish in color becoming light purple in color with development; and good garden performance.

2 Drawing Sheets

Botanical designation: *Osteospermum ecklonis.*
Cultivar denomination: 'Sunny Bianca'.

BACKGROUND OF THE INVENTION

The present invention relates to a new and distinct cultivar of *Osteospermum* plant, botanically known as *Osteospermum ecklonis,* and hereinafter referred to by the name 'Sunny Bianca'.

The new *Osteospermum* is a product of a planned breeding program conducted by the Inventor in Odense, Denmark. The objective of the program is to create and develop new *Osteospermum* cultivars with compact and uniformly mounded plant habit, freely flowering habit and attractive inflorescence coloration.

The new *Osteospermum* originated from a cross-pollination by the Inventor in May, 2003 of a proprietary selection of *Osteospermum ecklonis* identified as code number 50.003.00, not patented, as the female, or seed, parent with the *Osteospermum ecklonis* cultivar Sunny Caroline, not patented, as the male, or pollen, parent. The new *Osteospermum* was discovered and selected by the Inventor as a single flowering plant within the progeny of the stated cross-pollination in a controlled environment in Odense, Denmark in July, 2004.

Asexual reproduction of the new *Osteospermum* by terminal cuttings in a controlled environment in Odense, Denmark since January, 2005, has shown that the unique features of this new *Osteospermum* are stable and reproduced true to type in successive generations.

SUMMARY OF THE INVENTION

The cultivar Sunny Bianca has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Sunny Bianca'. These characteristics in combination distinguish 'Sunny Bianca' as a new and distinct cultivar of *Osteospermum:*

1. Upright and mounded plant habit.
2. Freely branching growth habit.
3. Freely flowering habit.
4. Daisy-type inflorescences with oblanceolate-shaped ray florets that are initially whitish in color becoming light purple in color with development.
5. Good garden performance.

In side-by-side comparisons conducted in Odense, Denmark, plants of the new *Osteospermum* differ from plants of the female parent selection primarily in ray floret color as plants of the female parent selection have dark purple-colored ray florets.

In side-by-side comparisons conducted in Odense, Denmark, plants of the new *Osteospermum* differ from plants of the male parent, the cultivar Sunny Caroline, in the following characteristics:

1. Plants of the new *Osteospermum* are taller and more vigorous than plants of the cultivar Sunny Caroline.
2. Plants of the new *Osteospermum* and the cultivar Sunny Caroline differ in ray floret coloration as plants of the cultivar Sunny Caroline have light pink-colored ray florets.

Plants of the new *Osteospermum* can be compared to plants of the *Osteospermum* cultivar Sunny Elizabeth, disclosed in U.S. Plant Pat. No. 16,564. In side-by-side comparisons conducted in Odense, Denmark, plants of the new *Osteospermum* differed from plants of the cultivar Sunny Elizabeth primarily in ray floret color as plants of the cultivar Sunny Elizabeth had pink-colored ray florets with purple-colored stripes. In addition, the lower surface of the ray florets of the new *Osteospermum* were yellow in color whereas the lower surface of the ray florets of the cultivar Sunny Elizabeth were pink in color.

BRIEF DESCRIPTION OF THE PHOTOGRAPHS

The accompanying photographs illustrate the overall appearance of the new *Osteospermum*. This photographs shows the colors as true as it is reasonably possible to obtain in colored reproductions of this type. Colors in the photographs may differ slightly from the color values cited in the detailed botanical description which accurately describe the colors of the new *Osteospermum*.

The photograph on the first sheet comprises a side perspective view of a typical flowering plant of 'Sunny Bianca'.

The photograph at the top of the second sheet is a close-up view of a typical developing inflorescence (left) and a typical fully developed inflorescence (right) of 'Sunny Bianca'.

The photograph at the bottom of the second sheet is a close-up view of the upper surface of a typical leaf of 'Sunny Bianca'.

DETAILED BOTANICAL DESCRIPTION

In the following description, color references are made to The Royal Horticultural Society Colour Chart, 2001 Edition, except where general terms of ordinary dictionary significance are used. The aforementioned photograph, following observations and measurements describe plants grown in De Lier, The Netherlands during the spring in a glass-covered greenhouse and under conditions and practices which approximate those generally used in commercial *Osteospermum* production. During the production of the plants, day temperatures ranged from 10° C. to 20° C., night temperatures averaged 10° C. and light levels ranged from 200 to 800 watts per square meter. Measurements and numerical values represent averages for typical flowering plants. Plants were pinched one time and were about 15 weeks old when the photographs and description were taken.

Botanical classification: *Osteospermum ecklonis* cultivar Sunny Bianca.

Parentage:

*Female, or seed, parent.*—Proprietary selection of *Osteospermum ecklonis* identified as code number 50.003.00, not patented.

*Male, or pollen, parent.*—*Osteospermum ecklonis* cultivar Sunny Caroline, not patented.

Propagation:

*Type.*—Terminal vegetative cuttings.

*Time to initiate roots, summer.*—About ten days at 18° C.

*Time to initiate roots, winter.*—About twelve days at 18° C. to 20° C.

*Time to produce a rooted cutting, summer.*—About three weeks at 18° C. to 20° C.

*Time to produce a rooted cutting, winter.*—About four weeks at 18° C.

*Root description.*—Medium in thickness, fibrous; white in color.

*Rooting habit.*—Freely branching; moderately dense.

Plant description:

*Plant form/growth habit.*—Upright and mounded plant habit. Inflorescences positioned above the foliar plane. Low to moderately vigorous growth habit.

*Plant height.*—About 17.2 cm.

*Plant diameter.*—About 16.3 cm.

*Lateral branches.*—Quantity per plant: Freely branching, about five lateral branches per plant. Length: About 7.1 cm. Diameter: About 4 mm. Internode length: About 4.5 mm. Strength: Strong. Texture: Smooth, glabrous. Color: 144A to 144B.

*Foliage description.*—Arrangement: Alternate, simple; sessile. Length: About 6.1 cm. Width: About 2.9 cm. Shape: Obovate. Apex: Broadly acute. Base: Cuneate. Margin: Dentate; coarse. Texture, upper and lower surface: Smooth, glabrous; leathery; densely pubescent along the leaf margins. Venation pattern: Pinnate. Color: Developing foliage, upper surface: Between 141B and 143A. Developing foliage, lower surface: Slightly darker than 144A. Fully expanded foliage, upper surface: Between 139A and 147A; venation, 145A to 145B. Fully expanded foliage, lower surface: 137A to 137B; venation, 145A.

Inflorescence description:

*Appearance.*—Daisy-type inflorescence form with oblanceolate-shaped ray florets. Inflorescences positioned above the foliage, arising from leaf axils. Disc and ray florets developing acropetally on a capitulum. Inflorescences face mostly upright to outward. Freely flowering habit; about 45 inflorescences develop over time per plant. Inflorescences not persistent. Inflorescences faintly fragrant.

*Flowering response.*—In northern Europe, plants of the new *Osteospermum* flower continuously from spring to late summer. Early flowering habit, plants begin flowering about eight weeks after pinching. Inflorescences last about two weeks on the plant.

*Inflorescence bud.*—Height: About 1.5 cm. Diameter: About 1.3 cm. Shape: Ovate. Color: Towards the base, 137B; towards the apex, 151A to 151B.

*Inflorescence size.*—Diameter: About 6.2 cm. Depth (height): About 1.8 cm. Disc diameter: About 6 mm. Receptacle diameter: About 9 mm. Receptacle height: About 4 mm.

*Ray florets.*—Shape: Oblanceolate. Length: About 3.1 cm. Width: About 1 cm. Apex: Retuse. Base: Attenuate. Margin: Entire. Texture: Smooth, glabrous; at the base, pubescent. Number of ray florets per inflorescence: About 20 in about two whorls. Color: When opening, upper surface: Close to 158C to 158D; towards the margin, close to 154D. When opening, lower surface: Close to 2A to 2B; central stripe, close to 197B to 197C. Fully opened, upper surface: Close to 75A; towards the apex, close to 75B; at the apex, close to 154D; towards the base, close to 77B. Fully opened, lower surface: Close to 12B; stripes, close to 200C.

*Disc florets.*—Shape: Tubular; apex dentate, five-pointed. Length: About 8 mm. Diameter, apex: About 3 mm. Diameter, base: About 0.9 mm. Number of disc florets per inflorescence: About 110. Color: Immature: Close to 198A to 198B; towards the apex, 98D. Mature: Apex: Close to 98D to 155A. Mid-section and base: Close to 155D.

*Phyllaries.*—Quantity per inflorescence: About 20. Length: About 9 mm. Width: About 2 mm. Shape: Lanceolate. Apex: Elongated acuminate. Base: Cuneate. Margin: Entire. Texture, upper and lower surfaces: Sparsely pubescent. Color, upper surface: 146B. Color, lower surface: 137B; towards the base, 138A.

*Peduncles.*—Length: About 6.2 cm. Diameter: About 2 mm. Strength: Strong. Aspect: Mostly upright to about 30° from vertical. Texture: Sparsely pubescent. Color: 144A.

*Reproductive organs.*—Androecium: Present on disc florets only. Anther shape: Narrowly oblong. Anther length: About 2 mm. Anther color: 202A. Pollen amount: Abundant. Pollen color: 21A. Gynoecium: Present on both ray and disc florets. Pistil length: About 4 mm. Stigma shape: Lanceolate. Stigma color: N186B. Style length: About 2 mm. Style color: 155A. Ovary color: 145D.

*Seeds/fruits.*—Seed and fruit development have not been observed on plants of the new *Osteospermum.*

Disease/pest resistance: Plants of the new *Osteospermum* have not been shown to be resistant to pathogens and pests common to *Osteospermums.*

Garden performance: Plants of the new *Osteospermum* have been observed to have good garden performance and to tolerate rain, wind and temperatures ranging from about −4° C. to about 40° C.

It is claimed:

1. A new and distinct *Osteospermum* plant named 'Sunny Bianca' as illustrated and described.

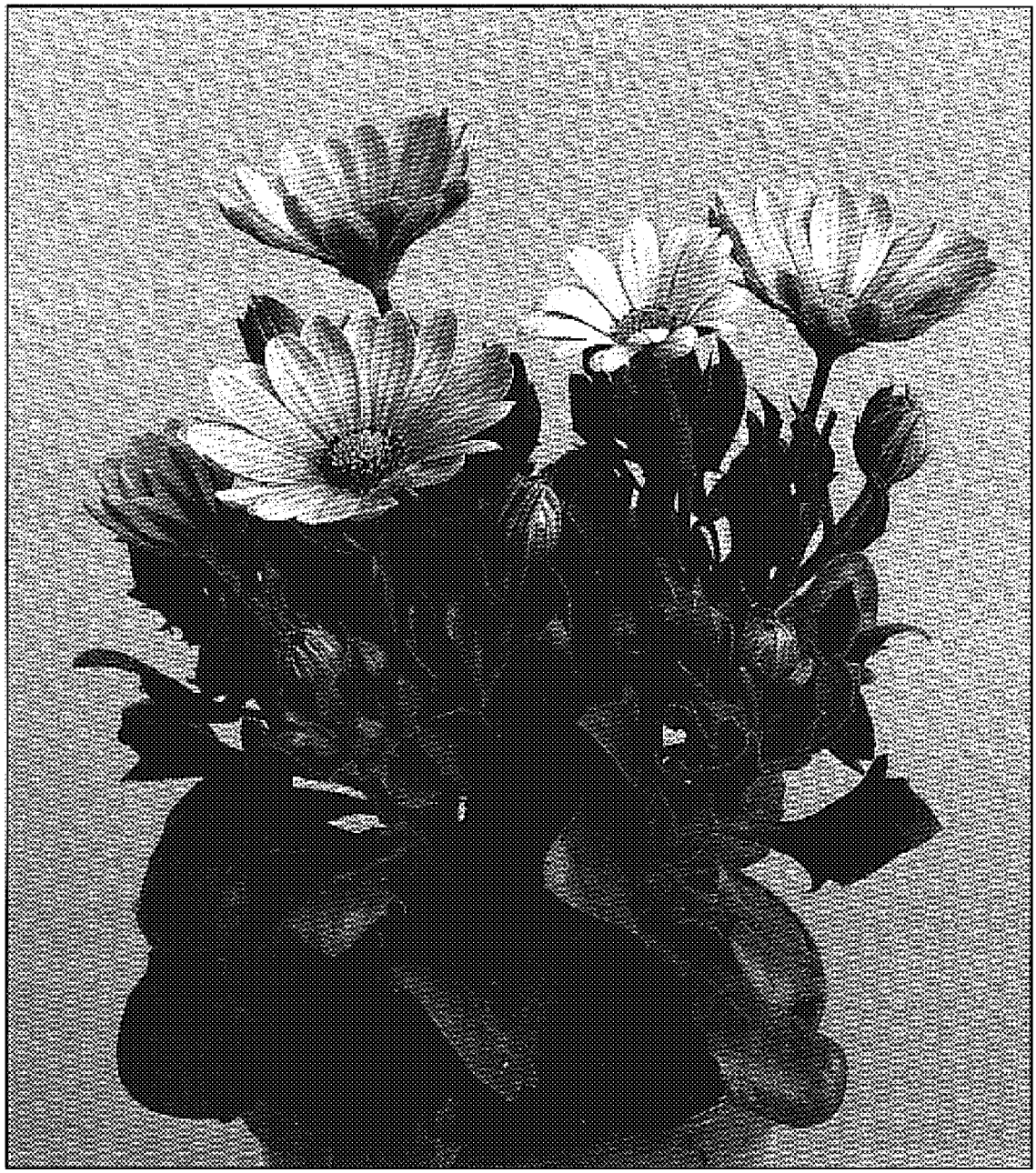

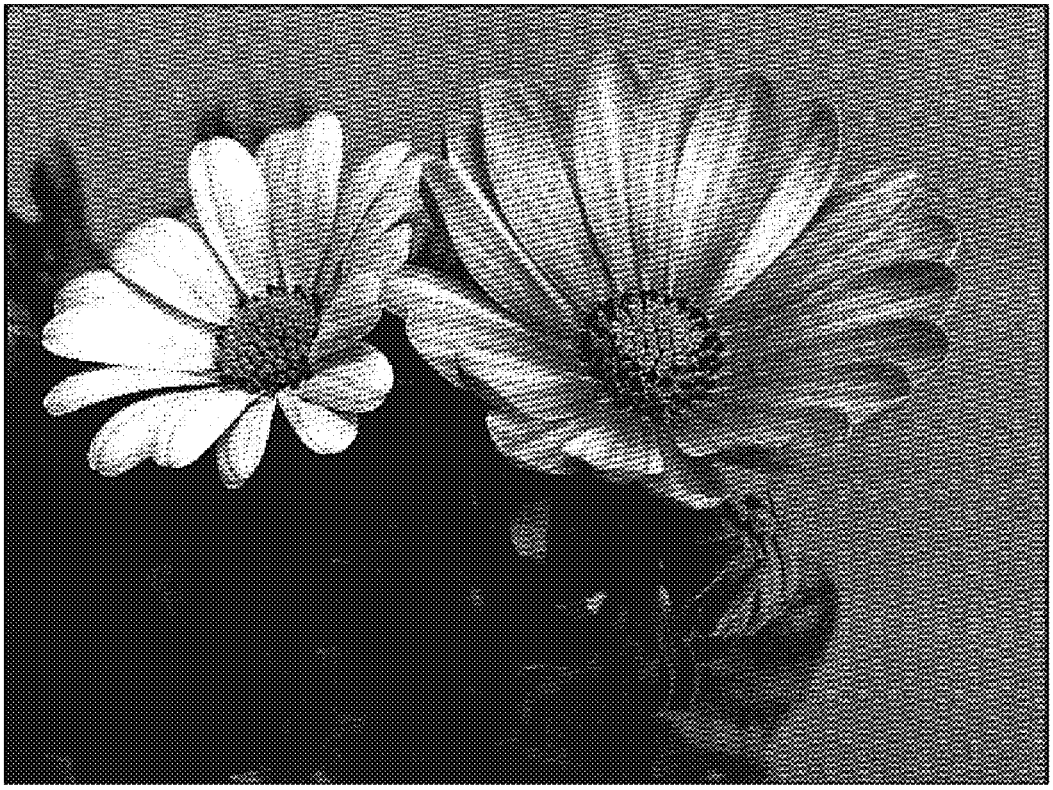
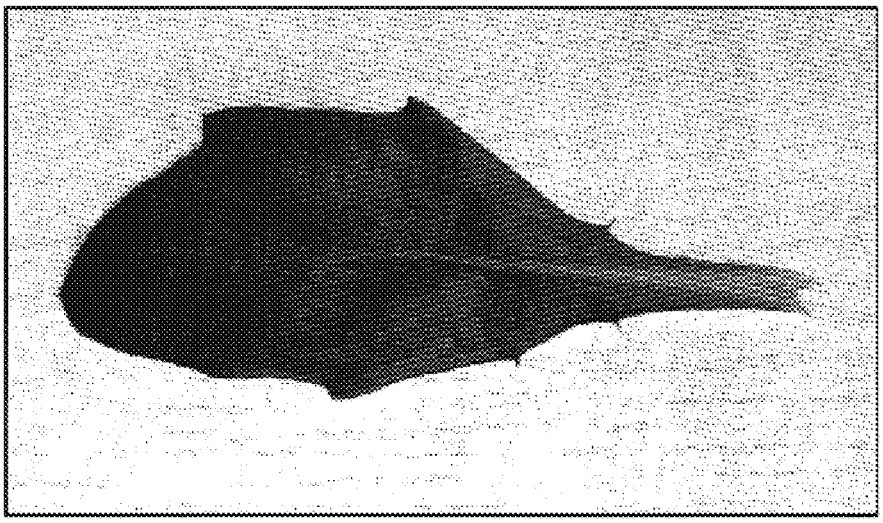

* * * * *